United States Patent
Rieber et al.

(10) Patent No.: US 8,337,510 B2
(45) Date of Patent: Dec. 25, 2012

(54) MEDICAL INSTRUMENT

(75) Inventors: Fabian Rieber, Stuttgart (DE);
Chi-Nghia Ho, Tubingen (DE);
Sebastian Schostek, Tubingen (DE);
Marc Oliver Schurr, Tubingen (DE)

(73) Assignee: Novineon Healthcare Technology Partners, GmbH, Tuebingen (DE)

( * ) Notice: Subject to any disclaimer, the term of this patent is extended or adjusted under 35 U.S.C. 154(b) by 682 days.

(21) Appl. No.: 11/830,339

(22) Filed: Jul. 30, 2007

(65) Prior Publication Data
US 2008/0033451 A1 Feb. 7, 2008

(30) Foreign Application Priority Data

Aug. 1, 2006 (DE) .................. 10 2006 000 382

(51) Int. Cl.
*A61B 17/24* (2006.01)
*A61B 17/26* (2006.01)

(52) U.S. Cl. .................. 606/114; 606/113; 606/110

(58) Field of Classification Search .................. 606/114, 606/200, 190, 46, 151, 192, 108, 153, 213, 606/128, 113, 127, 47, 264, 110; 623/1.11, 623/23.35, 1.15, 1.34, 23.65; 600/562, 37, 600/564, 371; 53/473, 476
See application file for complete search history.

(56) References Cited

U.S. PATENT DOCUMENTS

| 4,137,920 | A * | 2/1979 | Bonnet | 606/171 |
| 5,354,303 | A * | 10/1994 | Spaeth et al. | 606/128 |
| 5,735,289 | A * | 4/1998 | Pfeffer et al. | 600/564 |
| 6,920,840 | B1 * | 7/2005 | Sloan et al. | 119/14.47 |
| 2004/0138587 | A1 * | 7/2004 | Lyons, IV | 600/562 |
| 2005/0090858 | A1 * | 4/2005 | Pavlovic | 606/200 |

* cited by examiner

*Primary Examiner* — Victor Nguyen
*Assistant Examiner* — Tin Nguyen
(74) *Attorney, Agent, or Firm* — AlbertDhand LLP

(57) ABSTRACT

The invention is directed to an endoscopic retrieval instrument for receiving and retrieving one or more objects from the human body, the instrument comprising an insertion instrument, a retrieval container, and a coupling mechanism configured to selectively disconnect the retrieval container from the insertion instrument.

18 Claims, 10 Drawing Sheets

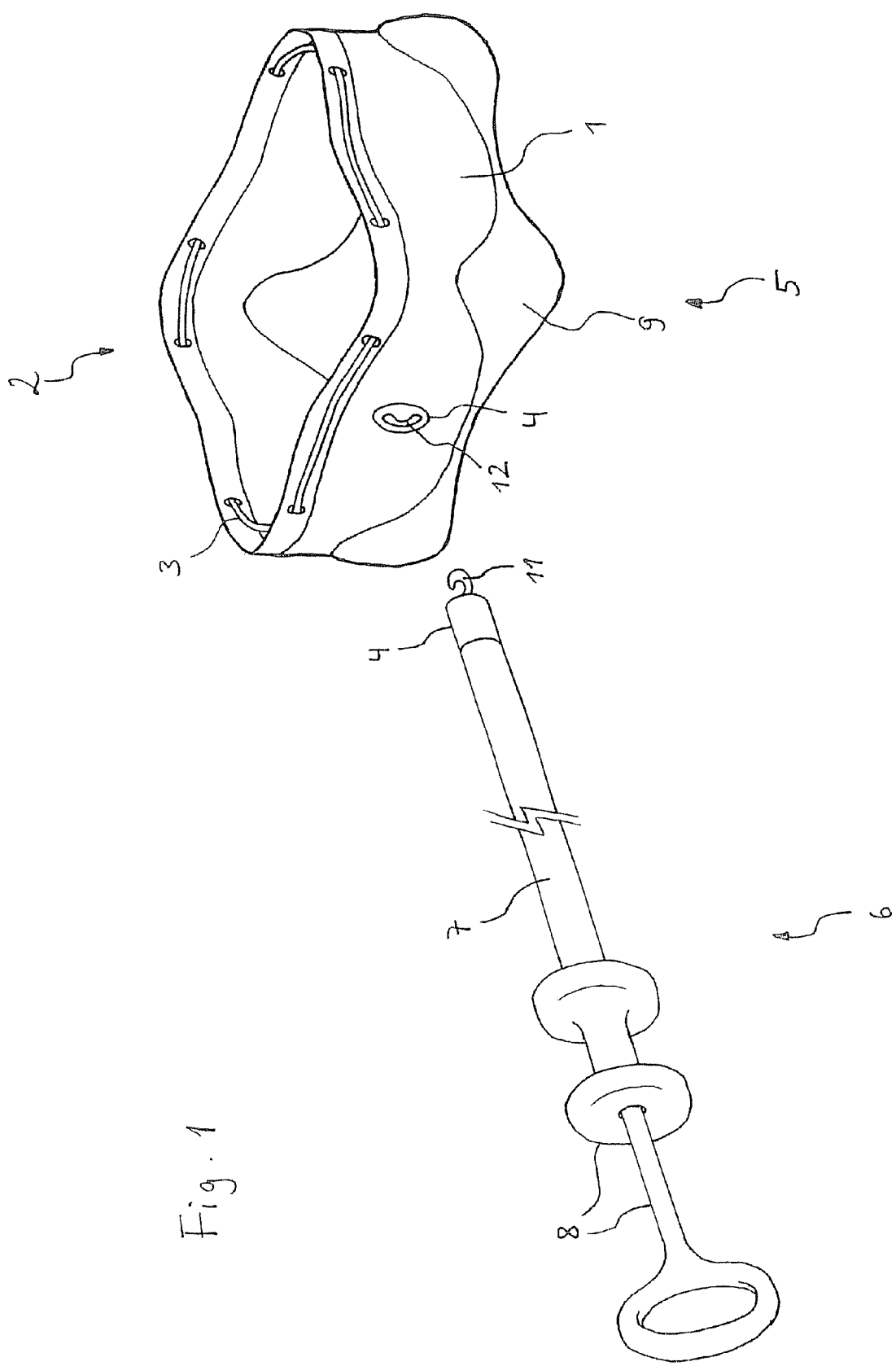

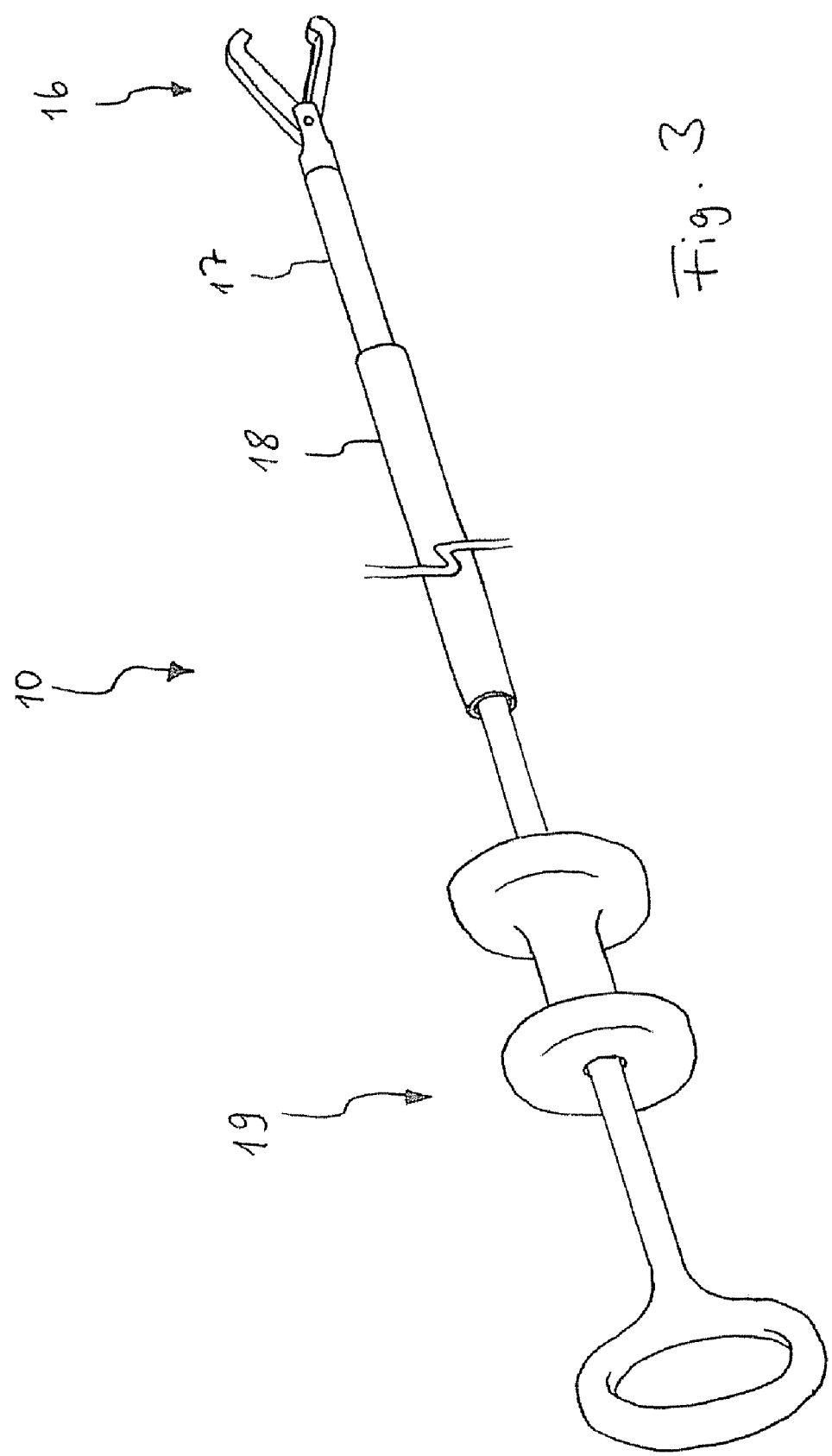

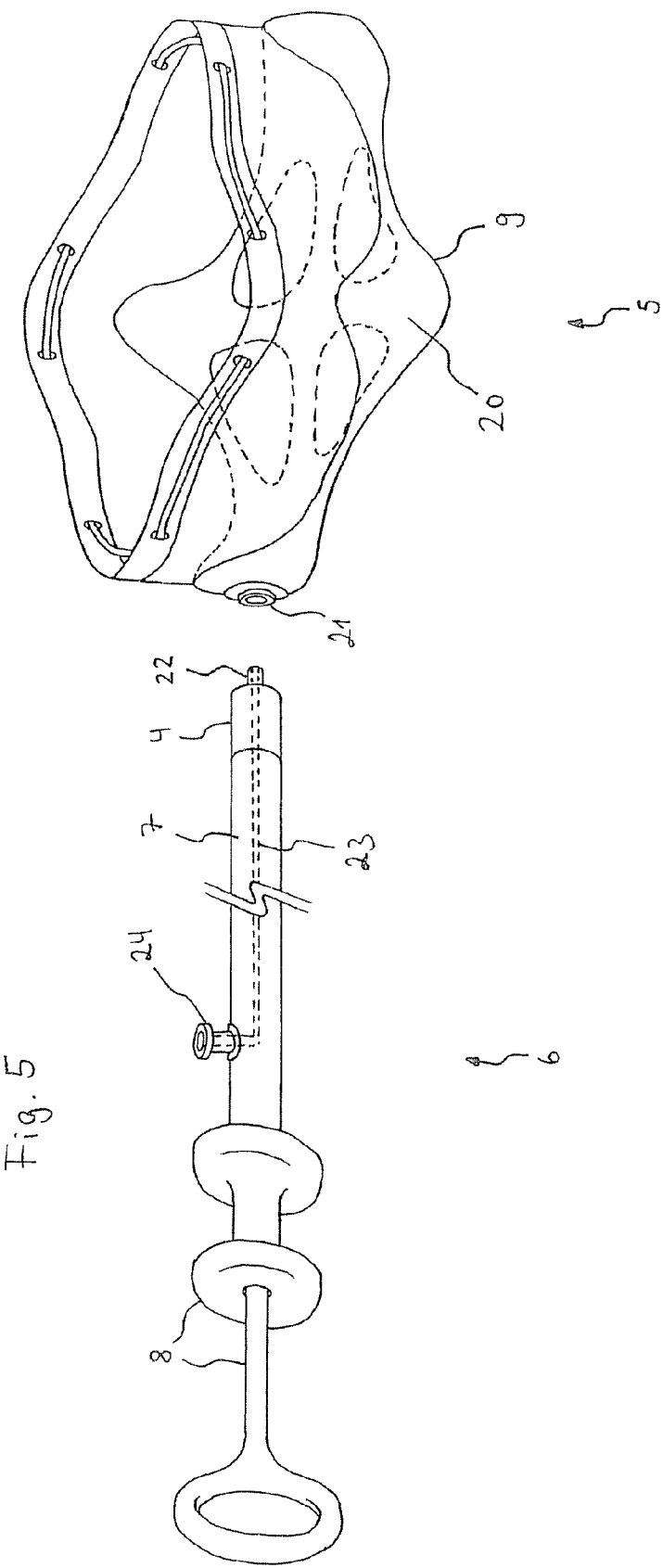

_US 8,337,510 B2_

MEDICAL INSTRUMENT

CROSS-REFERENCE TO RELATED APPLICATION

The present application claims priority to German Patent Application No. DE 102006000382.9, filed on Aug. 1, 2006, the entire disclosure of which is hereby incorporated by reference, to the extent that it is not conflicting with the present application.

BACKGROUND

In gastrointestinal endoscopy where flexible endoscopes are used, foreign bodies or pieces of tissue are usually secured by means of a grasping instrument such as a forceps or snare applied through the working channel of the flexible endoscope and are removed from the body by withdrawing the entire endoscope. In various cases also plural objects may be present in the intestinal tract, for instance subsequent to an endoscopic piecemeal mucosal resection where the surface mucosal layer of the wall of the intestinal tract (mucosa) is cut off in several pieces. Such cases would necessitate a repeated withdrawal and re-insertion of the flexible endoscope, since usually only one working channel is available for retrieval.

SUMMARY

The present invention is to provide a retrieval instrument capable of being used endoscopically so as to receive one or plural pieces of tissue or foreign bodies for retrieval from the human body.

This object is achieved by means of a retrieval instrument comprising. Since in gastrointestinal endoscopy where a flexible endoscope is used, often only one working channel is available, the retrieval container may be configured so as to be capable of being inserted into the body through the working channel by means of an insertion instrument and of being selectively decoupled from the insertion instrument. Decoupling the retrieval container from the insertion instrument allows insertion of a grasping instrument such as a forceps or snare through the working channel for placing the objects to be retrieved into the retrieval container.

BRIEF DESCRIPTION OF THE DRAWINGS

Hereinafter, the invention will be explained in detail by way of example embodiments, with reference to the accompanying drawings.

FIG. 1 is a schematic representation of a retrieval container including an insertion instrument;

FIG. 3 represents an application instrument;

FIG. 5 shows an embodiment of a retrieval container and an insertion instrument comprising a chamber system for receiving a fluid;

DETAILED DESCRIPTION

Figure 2A:
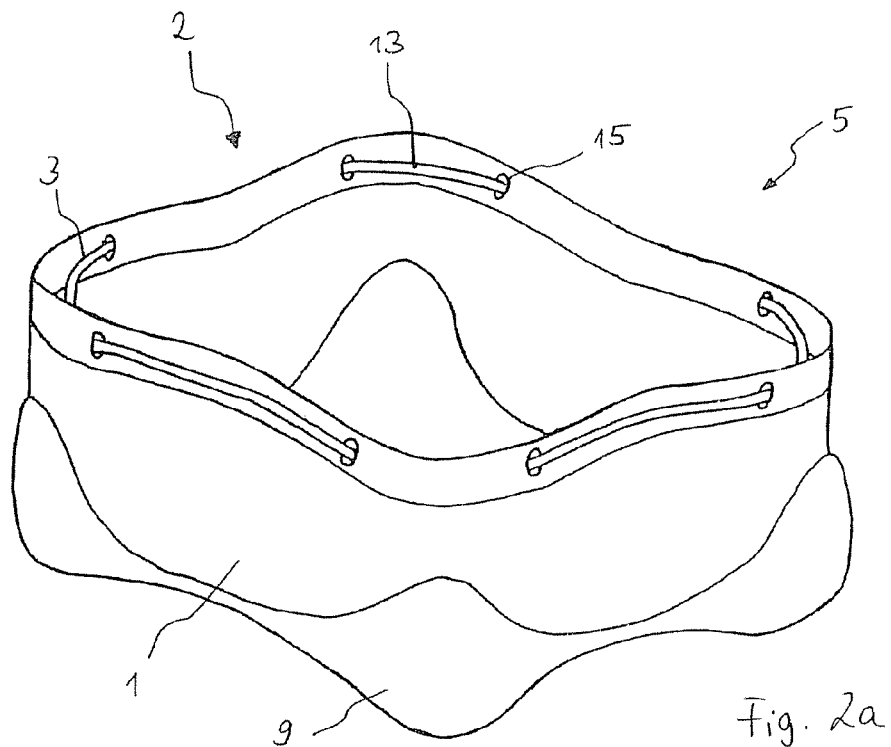
FIG. 2 represents embodiments of the closing member.

Endoscopy is a method used in medicine for visual representation of various inner regions of the human body employing an imaging system inserted into the body through artificial or natural access pathways. Endoscopic methods provide access to the abdominal cavity (laparoscopy), the pelvis (pelviscopy), the joints (arthroscopy), the respiratory tract (bronchoscopy) or the intestinal tract (gastrointestinal tract) for visual inspection, diagnostic examinations or surgical interventions. In general, endoscopic methods are much less traumatic for the patient than corresponding open surgery methods, since on the one hand access is gained through natural body openings (e.g. bronchoscopy, gastrointestinal endoscopy) or artificial access can be created via relatively small incisions ranging from a few millimeters to centimeters (e.g. laparoscopy, arthroscopy). Moreover, the introduction of endoscopic methods has opened up new diagnostic and therapeutical possibilities owing to a specifically developed instrumentation. What all endoscopic methods have in common is the use of a camera system and the presence of a transparent fluid in the operating space, e.g. gas (air or nitrogen or carbon dioxide) in laparoscopy, bronchoscopy and in gastrointestinal endoscopy or water in arthroscopy by means of which the volume of the operating space is kept open.

In various applications of endoscopic methods, it may become necessary to manipulate/handle pieces of tissue or foreign bodies that are loose in the body of the treated patient and are to be retrieved. These may for instance comprise resected organs or parts of organs in laparoscopy (gall bladder, appendix) or swallowed foreign bodies or resected tissue pieces subsequent to an endoscopic mucosal resection in the intestinal tract. In laparoscopy, devices for retrieval of tissue pieces are used, in particular various instruments comprising closeable bags or pouches as disclosed e.g. in U.S. Pat. No. 6,350,267, U.S. Pat. No. 6,409,267, U.S. Pat. No. 5,465,731 and US 2004/0138587 the entire disclosures of which are incorporated herein by reference, to the extent that they are not conflicting with the present application. Since in laparoscopic methods surgery is performed in sterile regions of the body, in laparoscopy a retrieval instrument has the particular function of minimizing or avoiding a contamination of the abdominal cavity with body tissue and body fluids capable of causing an inflammation of the abdominal cavity or with tumor cells that could lead to a relapse.

In gastrointestinal endoscopy where flexible endoscopes are used, foreign bodies or pieces of tissue are usually secured/grasped by means of a grasping instrument such as a forceps or snare applied through the working channel of the flexible endoscope and are removed from the body by withdrawing the entire endoscope. In various cases also plural objects may be present in the intestinal tract, for instance subsequent to an endoscopic piecemeal mucosal resection where the surface mucosal layer of the wall of the intestinal tract (mucosa) is cut off in several pieces. Such cases would necessitate a repeated withdrawal and re-insertion of the flexible endoscope, since usually only one working channel is available for retrieval.

As shown, for example, in FIG. 1, the invention contemplates a retrieval container 5 capable of being inserted endoscopically so as to receive one or more pieces of tissue or foreign bodies for retrieval from the human body. Since often only one working channel is available in gastrointestinal endoscopy where a flexible endoscope is used, the retrieval container 5 may be configured so as to be capable of being inserted into the body through the working channel by means of an insertion instrument 6 and/or capable of being selectively decoupled from the insertion instrument 6. Decoupling the retrieval container 5 from the insertion instrument 6 allows insertion of a grasping instrument such as a forceps or snare through the working channel for placing the objects to be retrieved into the retrieval container 5. The retrieval container 5 may comprise various devices and structures which facilitate/promote shaping for easy filling of the retrieval container 5 and/or stabilize the retrieval container 5 in a desired orientation. In addition, the retrieval container 5 may comprise a closing member 3 enabling the retrieval container 5 to be selectively closed such that objects contained in the retrieval container 5 cannot fall out of the retrieval container 5.

The depicted medical instrument includes a retrieval container 5 for receiving objects loose in the human body and an insertion instrument 6 for inserting the retrieval container 5 into the human body and, optionally, an application instrument 10 by means of which the retrieval container 5 can be closed and/or removed from the human body.

The depicted retrieval container 5 includes at least one opening 2 through which the objects to be retrieved can reach the container 1 of the retrieval container 5. The opening 2 of the retrieval container 5 may include a closing member 3 enabling the retrieval container 5 to be selectively closed. After closure of the retrieval container 5, the objects to be retrieved are enclosed inside the container 1 of the retrieval container 5. The depicted retrieval container 5 further includes a structuring member 9 capable of selectively facilitating/promoting the retrieval container 5 to assume a shape that facilitates filling the container 1. The depicted insertion instrument 6 includes a shaft 7 which may be configured to allow insertion of the insertion instrument 6 into a working channel of a flexible endoscope. In addition, the illustrated medical instrument includes a connecting device 4 having connecting members 11,12 capable of being selectively connected in order to selectively connect the insertion instrument 6 to the retrieval container 5. Further, the insertion instrument 6 may include an operating member 8 that may be actuated to allow setting/operating of the connecting device 4. In one embodiment, actuation of the operating member 8 causes the retrieval container 5 to be decoupled from the insertion instrument 6, as shown in FIG. 1.

During insertion of the retrieval container 5 through the working channel of a flexible endoscope, the retrieval container 5 may be provided in a folded state. Subsequent to insertion of the retrieval container 5, the retrieval container 5 is unfolded. A structuring member 9 may be provided to bias the retrieval container 5 to assume a shape that facilitates filling the container 1.

In one embodiment, a closing member 3 for closing the opening 2 of the retrieval container 5 includes a cable or thread 13 which is passed through openings or apertures 15 in the outer wall of the retrieval container 5, as shown in FIG. 2a.

Figure 2B:
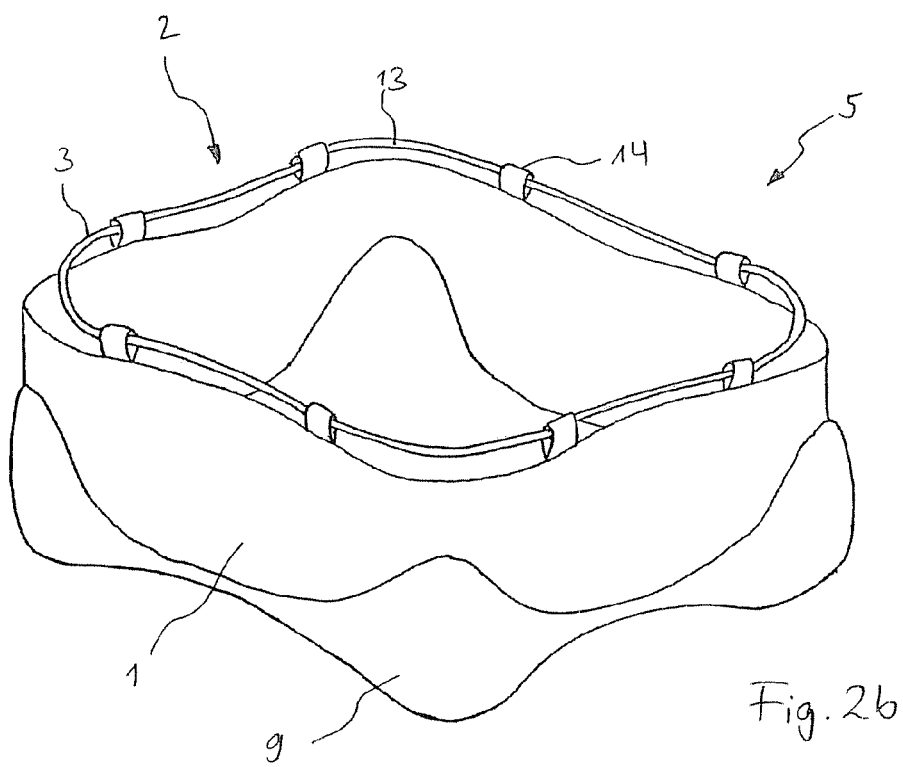

In another embodiment of the closing member 3 for closing the opening 2 of the retrieval container 5, the closing member 3 includes a thread 13 passed through loops 14 in the outer wall of the retrieval container 5, as shown in FIG. 2b.

In another embodiment of the application instrument 10, as shown in FIG. 3, the application instrument 10 includes a shaft 17 connected at its proximal end to an operating member 19 and at its distal end to a grasping device 16. Further, the shaft 17 of the illustrated application instrument 10 is guided in an outer tube 18. By actuating the operating member 19 the grasping function of the grasping device 16 can be set/performed. The outer tube 18 of the illustrated application instrument 10 is configured so as to be movable relative to the shaft 17.

Figure 4A:
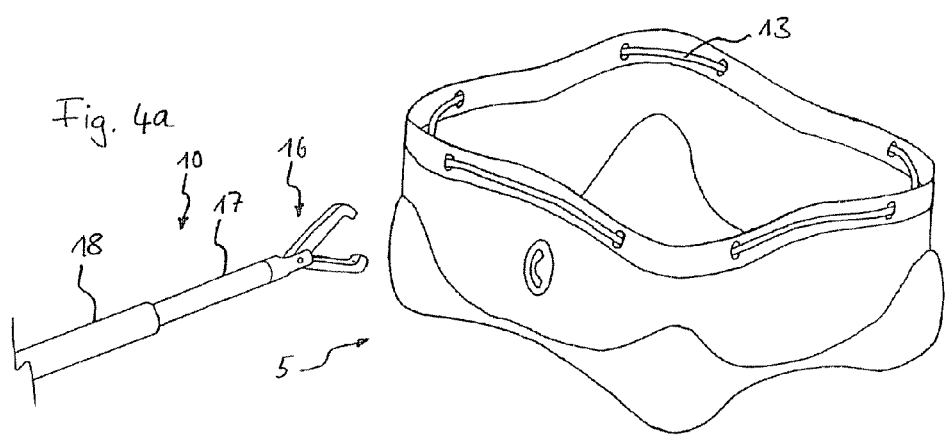
FIG. 4 illustrates a method for closing a retrieval container using the application instrument.
Figure 4B:
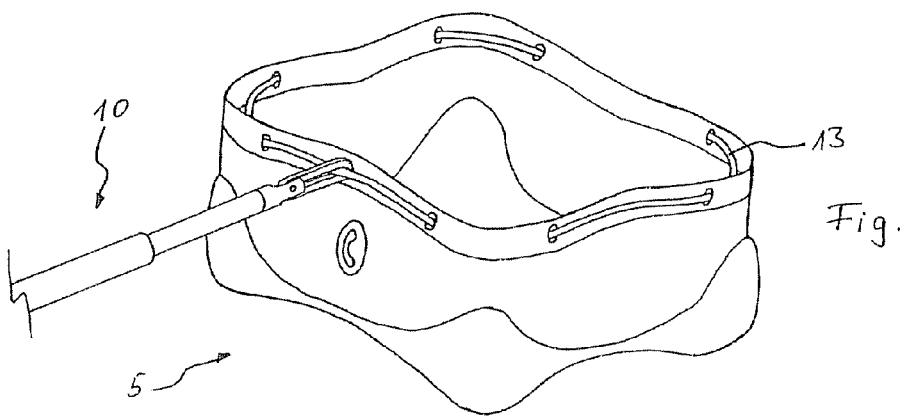
Figure 4C:
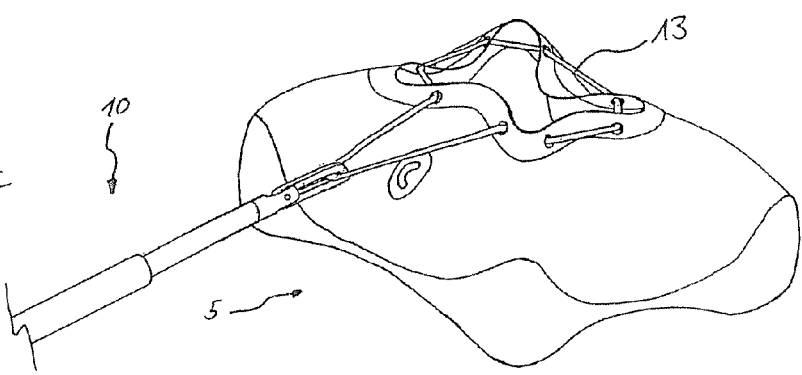
Figure 4D:
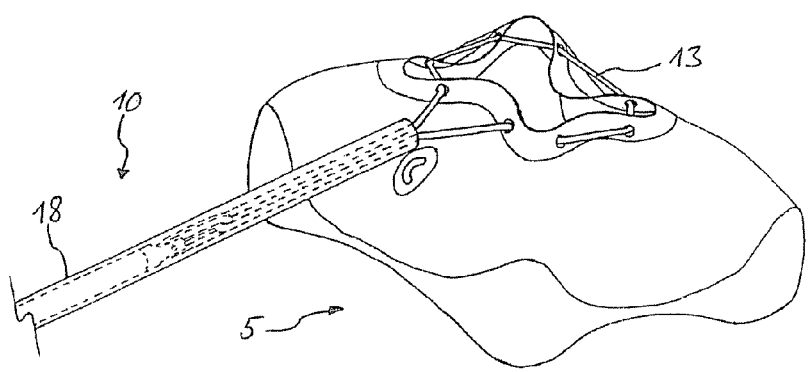

The application instrument 10 may be suitable for closing the opening 2 of the retrieval container 5. One such method for closing the opening 2 of the retrieval container 5 is illustrated in FIGS. 4a-4D and may include at least three steps. The application instrument 10 is brought close to the retrieval container 5, as shown in FIG. 4a. The thread 13 of the closing member 3 is grasped by means of the grasping device 16 of the application instrument 10, as shown in FIG. 4b. Pulling back the application instrument 10 causes the opening 2 to be closed, as shown in FIG. 4c. For supporting closure of the opening 2 of the retrieval container 5, the outer tube 18 is moved/pushed forward over the grasping device 16 or the grasping device 16 is pulled into the outer tube 18. Thus, the reaction force acting on the retrieval container 5 caused by pulling back the thread 13 can be reduced, as shown in FIG. 4d.

In one embodiment of the retrieval container 5 and the insertion instrument 6, shown, for example, in FIG. 5, the structuring member 9 of the retrieval container 5 includes of a chamber system 20 capable of being filled with a fluid. Filling the chamber system 20 with a fluid enables the chamber system 20 to assume a predetermined shape that facilitates filling of the retrieval container 5 with objects such as pieces of tissue or foreign bodies. If a liquid such as water is used as fluid, the weight of the fluid can stabilize the positioning of the retrieval container 5. The illustrated chamber system 20 includes a valve 21 for filling the chambers. The valve 21 may be configured so as to retain a fluid contained in the chamber system 20 when it is not actuated. At a distal end thereof, the illustrated insertion instrument 6 includes a filler neck (port) 22 for filling the chamber system 20, the filler neck being capable of being coupled to the valve 21. The filler neck 22 is connected to a connection member 24 via a fluid conduit 23 located in the shaft 7 of the insertion instrument 6 so as to enable a fluid introduced into the fluid conduit 23 via the connection member 24 to exit from the filler neck 22. The filler neck 22 is configured so as to enable passage of a fluid through the valve 21 into the chamber system 20 by coupling the filler neck 22 to the valve 21. For filling the chamber system 20 with a fluid, the filler neck 22 of the insertion instrument 6 is coupled to the valve 21 of the retrieval container 5. A device such as, for example, a syringe is coupled to the connection member 24 to convey a fluid through the connection member 24, the fluid conduit 23, the filler neck 22 and the valve 21 into the chamber system 20.

In a further development of the insertion instrument 6 for filling the chamber system 20 with a fluid through the valve 21, the insertion instrument 6 may include a connecting device 4. The valve 21 is configured so as to enable the connecting device 4 to be mechanically coupled to the valve 21. In one such embodiment, by actuating the operating member 8 of the insertion instrument 6, the connection between the connecting device 4 and the valve 21 can selectively be disengaged.

In using the illustrated instrument, the retrieval container 5 may be inserted or applied through the working channel of a flexible endoscope (not shown). To this end, the retrieval container 5 can be folded such that it can be passed through the working channel of a flexible endoscope. In a folded state, the retrieval container 5 is mechanically connected at the valve 21 to the insertion instrument 6 via the connecting device 4. The folded retrieval container 5 is inserted at the insertion instrument 6 into the human body through the working channel of an endoscope. In the operating space, e.g. the stomach or colon, the retrieval container 5 can be unfolded by introducing a fluid into the chamber system 20. To facilitate correct orientation, the insertion instrument 6 may exhibit a marker indicating the orientation of the opening 2 of the retrieval container 5. After decoupling of the retrieval container 5 from the insertion instrument 6 by actuation of the operating member 8, the valve 21 is in a state in which the fluid contained in the chamber system 20 of the retrieval container 5 is retained by the valve 21.

Figure 6:
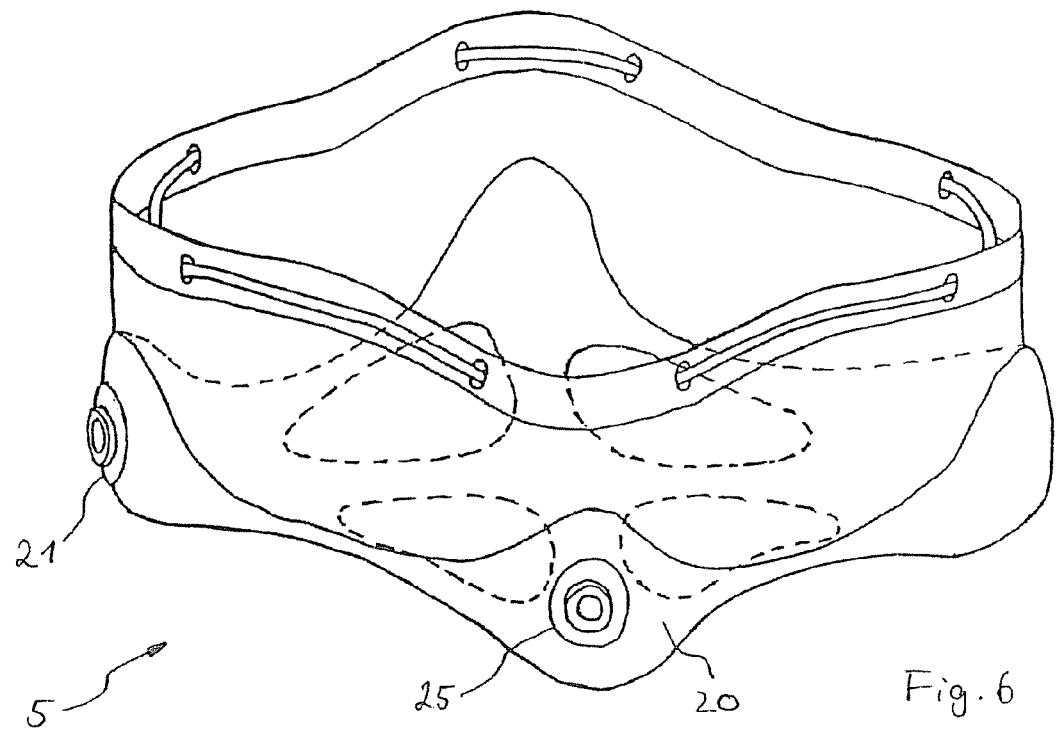
FIG. 6 shows an embodiment of a retrieval container comprising an outlet valve.

In another development of the retrieval container 5, as shown in FIG. 6, the retrieval container 5 may include an outlet valve 25. Actuation of the outlet valve 25 allows the fluid to exit the chamber system 20 thus causing the retrieval container 5 to collapse to facilitate removal from the human body.

Figure 7:
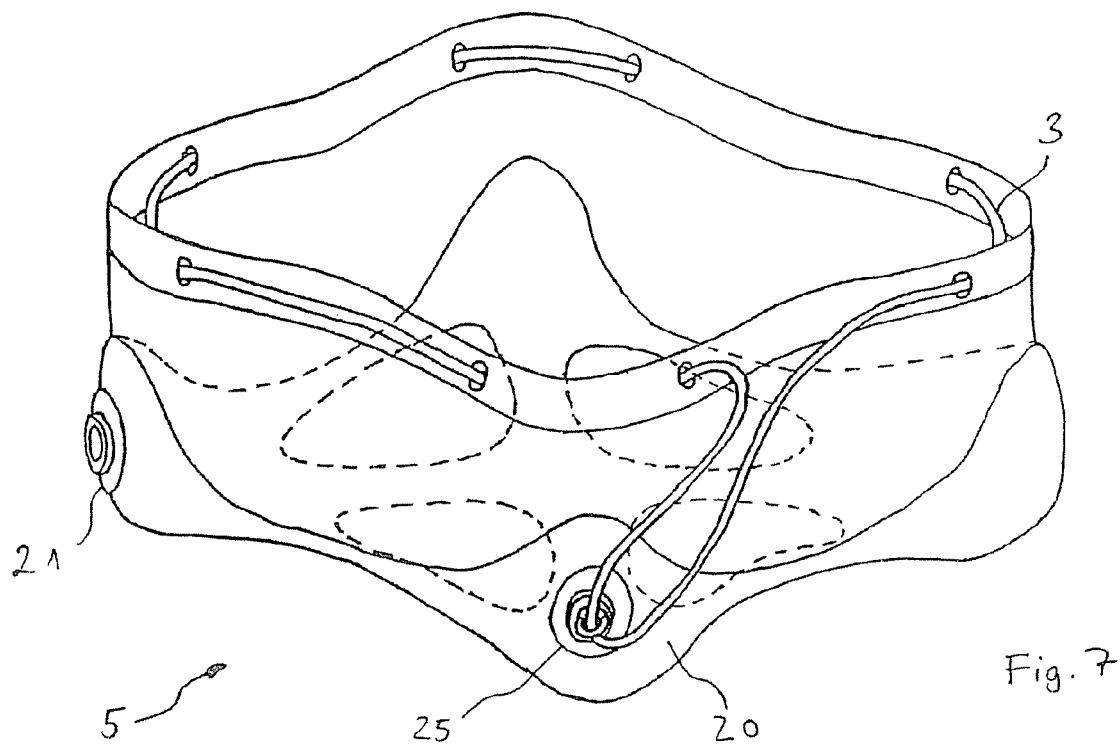
FIG. 7 shows an embodiment of an outlet valve.

In a further development of the retrieval container 5, as shown in FIG. 7, the retrieval container 5 may include an outlet valve 25 connected to a closing member 3 such that the discharge function of the outlet valve 25 can directly or indirectly be set via the closing member 3. Here, the instrument may be adapted such that upon closure of the retrieval container 5, the discharge function of the outlet valve 25 is automatically set to allow the fluid to exit from the chamber system 20. For example, the thread 13 of the closing member 3 may be connected to the outlet valve 25 such that pulling the thread 13 during closure of the retrieval container 5 causes the outlet valve 25 to be opened.

In an example embodiment of the retrieval container 5, the structuring member 9 includes a wire structure.

In another example embodiment of the retrieval container 5, the retrieval container 5 includes weights facilitating/promoting stabilization of the positioning of the retrieval container 5.

Figure 8:
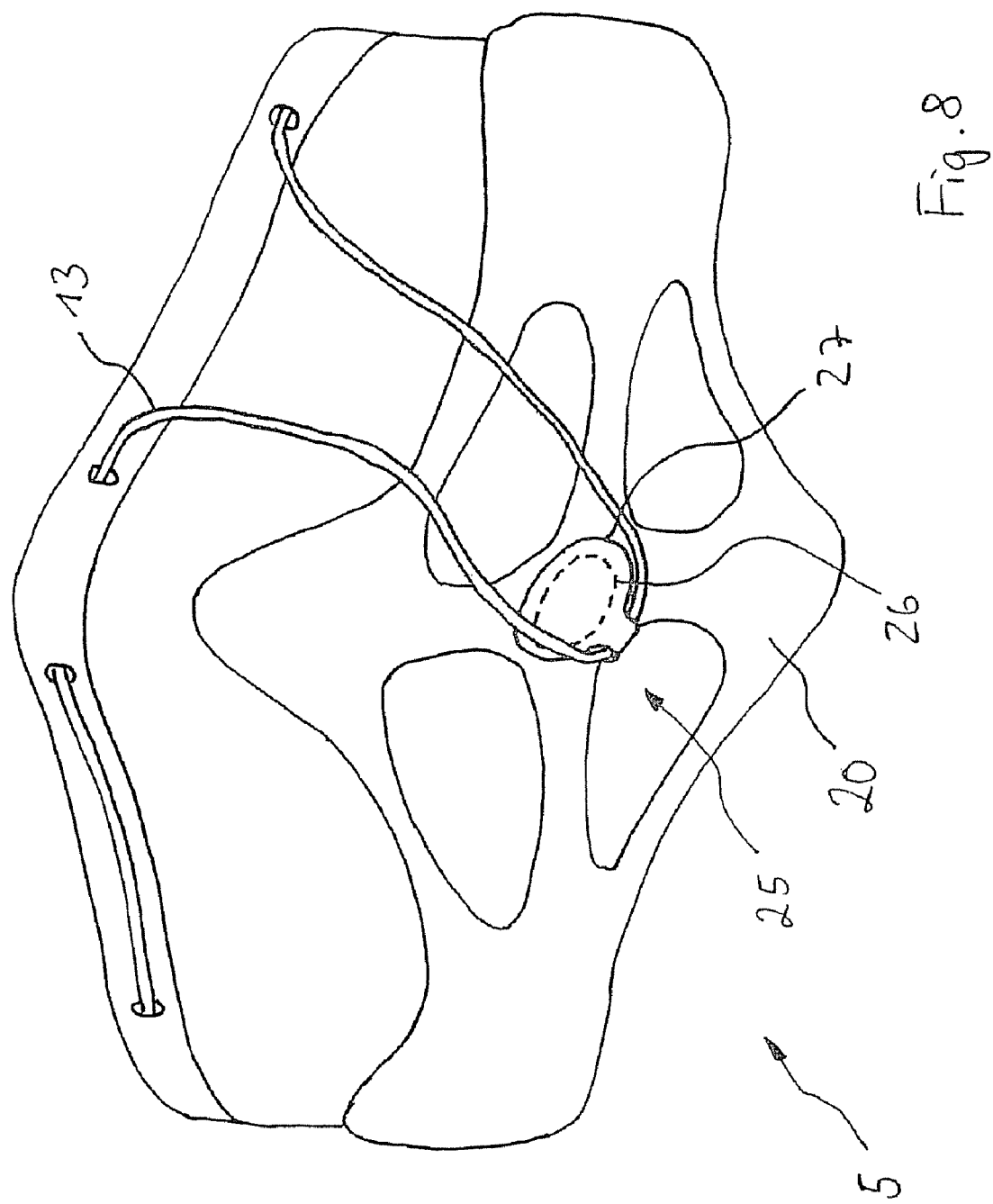
FIG. 8 shows an embodiment of an outlet valve.

In still another example embodiment, as shown in FIG. 8, the outlet valve 25 includes an outlet opening 26 in an outer wall of the chamber system 20, which can be sealed against the fluid using, for example, an adhesive sealing film 27. Here, the sealing film 27 may be connected to the thread 13 such that pulling the thread 13 upon closure of the retrieval container 5 causes the sealing film 27 to be pulled away from the outer wall of the chamber system 20, thus unblocking/opening the outlet opening 26.

Figure 9:
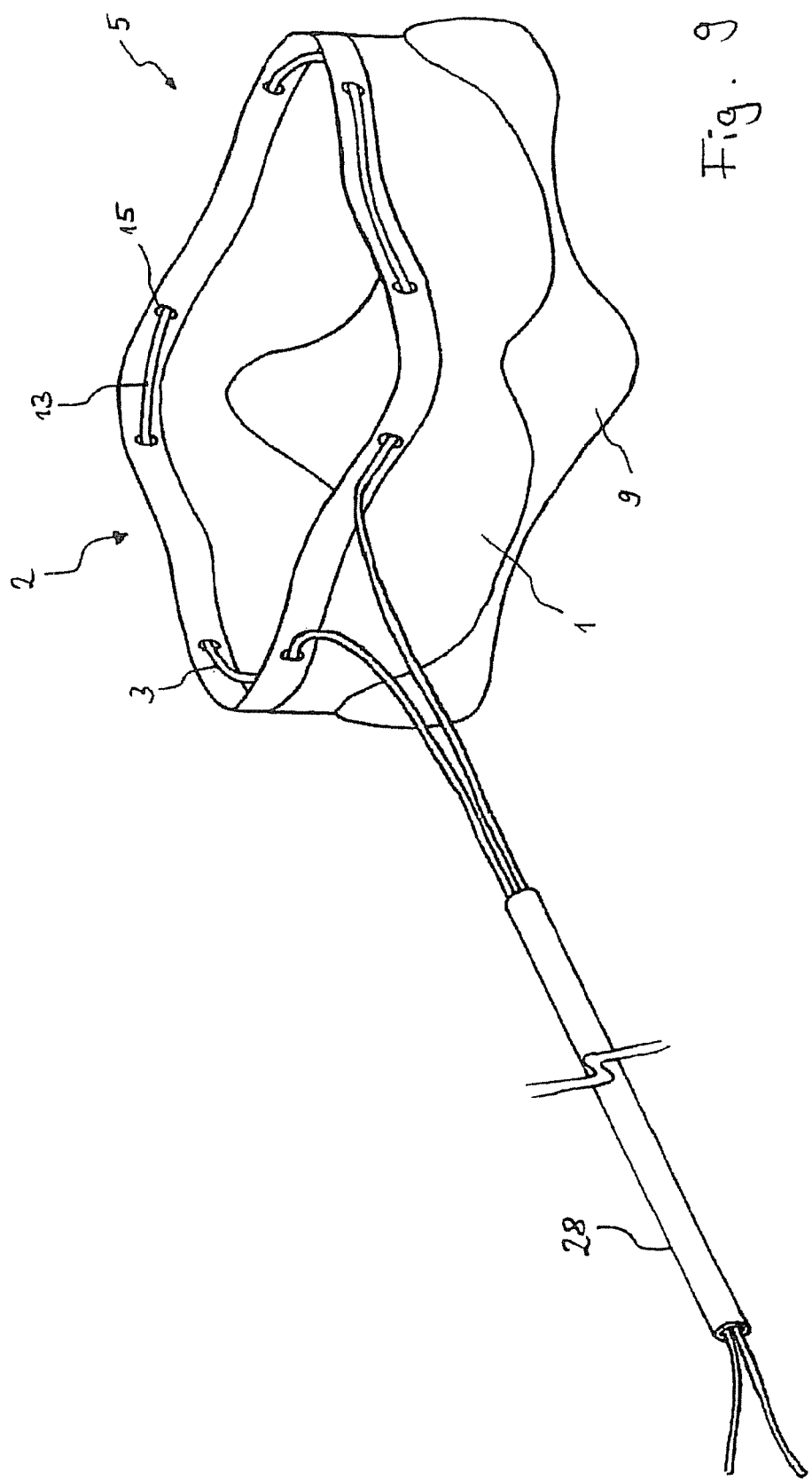
FIG. 9 shows an embodiment of a closing member.

In another example embodiment, as shown in FIG. 9, a thread 13 may be configured such that, subsequent to insertion of the retrieval container 5, the thread 13 may be guided out of the human body either through a working channel of a flexible endoscope or adjacent to the flexible endoscope alongside thereof. For closing the opening 2, a tube member 28 may be passed over/provided around the thread 13 and pushed forward towards the retrieval container 5.

Figure 10:
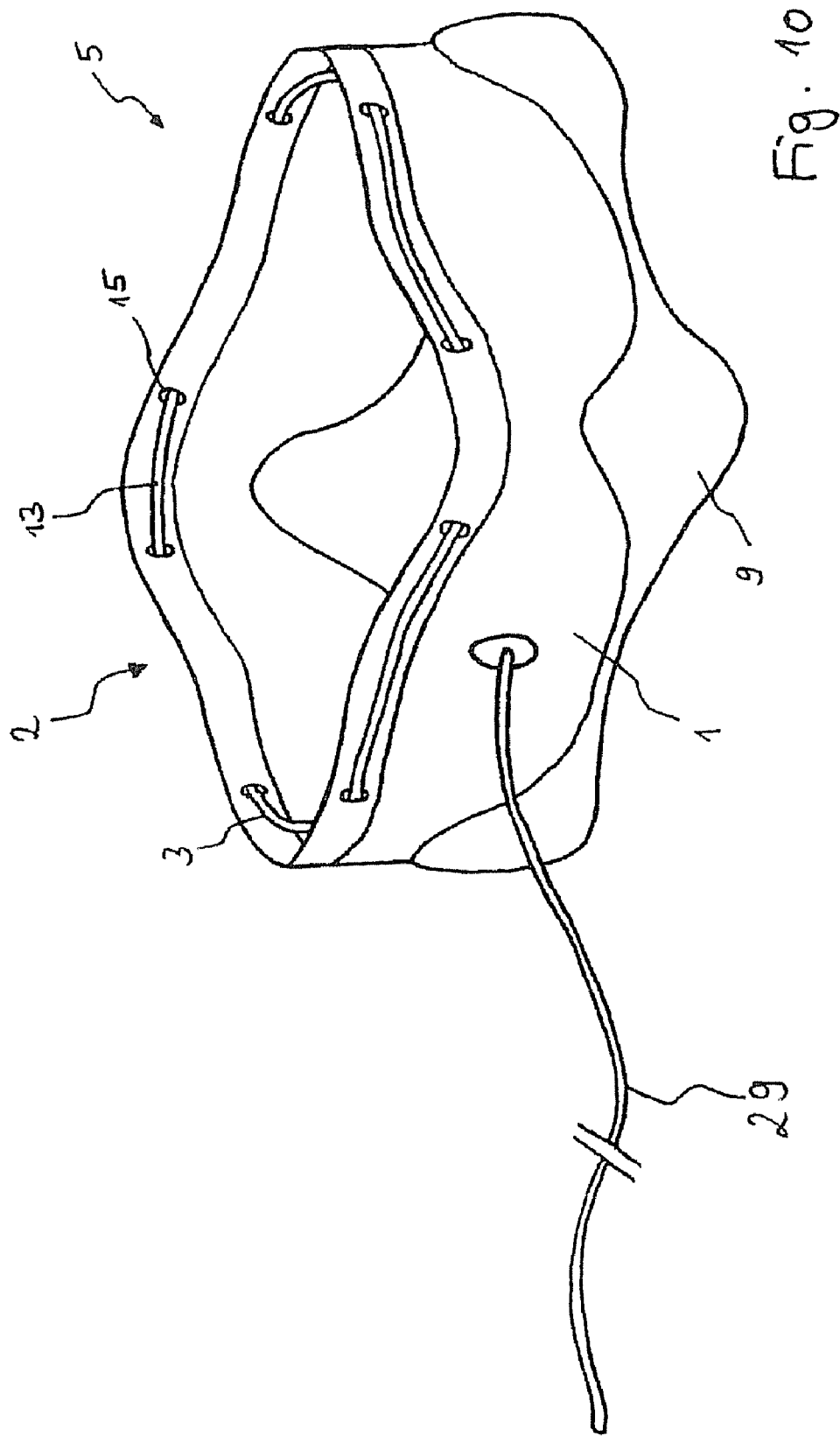
FIG. 10 shows an embodiment of a retrieval container.

Since the retrieval container 5 may be subject to peristalsis, in particular when used in gastrointestinal endoscopy, there is a risk that the retrieval container 5 dislocates. Therefore, in one embodiment, as shown in FIG. 10, a retrieval container 5 may include a fastening member or holding member 29, such as, for example, a thread, which may be guided out of the human body, for example, through the working channel of the flexible endoscope or adjacent to the flexible endoscope alongside thereof. This measure may allow the dislocation of the retrieval container 5 to be limited or controlled.

In endoscopy, the operating space is conventionally monitored through a monitor. In particular, monitoring or controlling gastrointestinal endoscopy orientation often proves to be difficult, since the endoscope may be rotated several times during this practice. Also, when using the retrieval container 5, the orientation of the retrieval container 5 relative to gravity is of importance. In one embodiment, the instrument may be configured to facilitate orienting the retrieval container 5 prior to unfolding of the retrieval container 5 such that the opening 2 of the retrieval container 5 faces upwards. Such an arrangement may be desirable where the opening of the retrieval container 5 may not be clearly identifiable from the folded retrieval container 5.

Figure 11:
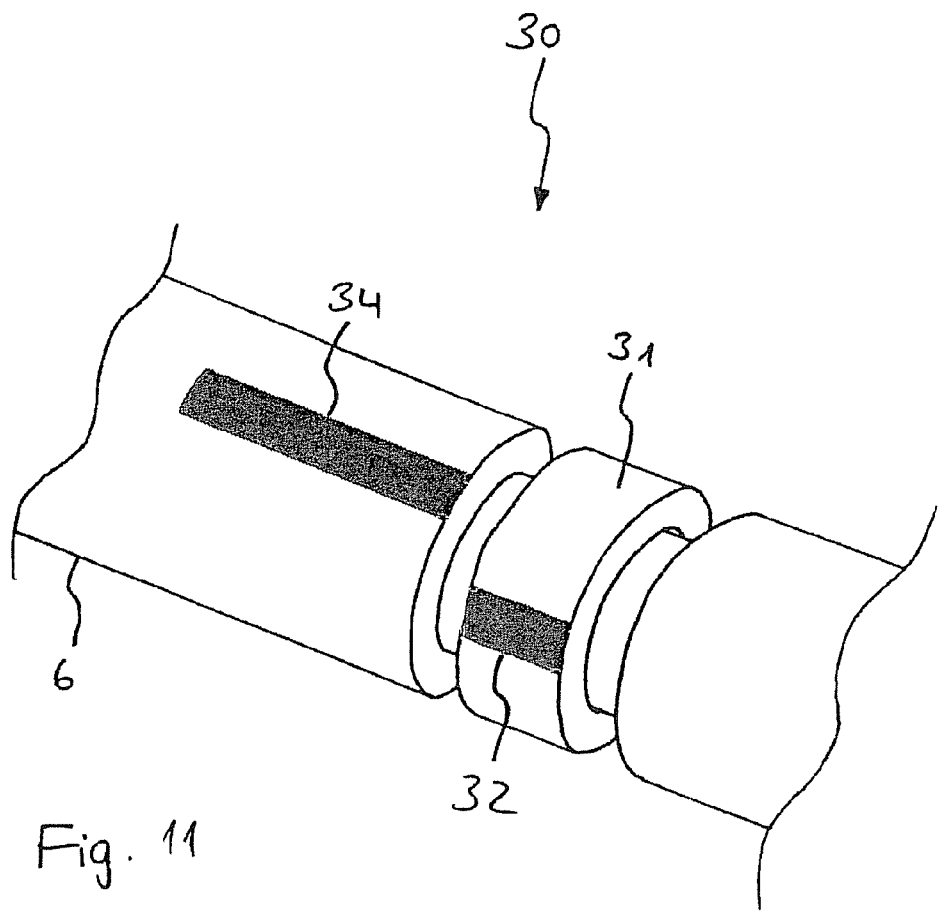
FIG. 11 represents an orienting device.
Figure 12:
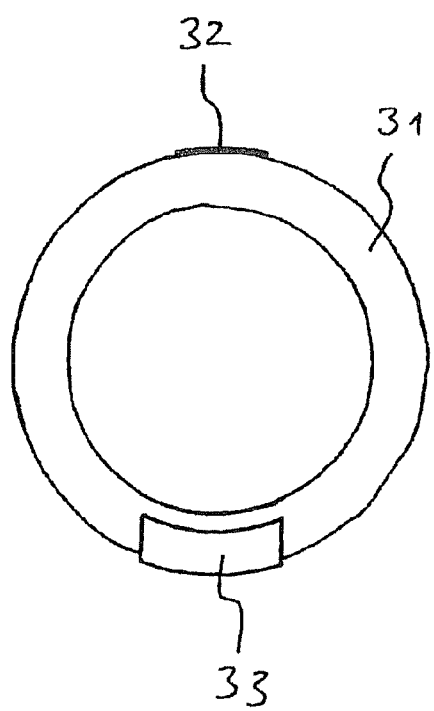
FIG. 12 represents an indicator ring.

In a further development of an example insertion instrument 6, as illustrated in FIGS. 11 and 12, the insertion instrument 6 may include an orienting device 30 which can indicate a suitable orientation of the retrieval container 5 (shown, for example, in FIGS. 2a and 2b). The illustrated orienting device 30 is located at a distal end of the insertion instrument 6, and includes an indicator ring 31 secured on the insertion instrument 6 so as to be freely rotatable about the axis of the insertion instrument 6. The indicator ring 31 includes a first marker 32 as well as an eccentrically positioned weight 33. The first marker 32 is located on the outside of the indicator ring 31. The weight 33 causes the indicator ring 31 to independently orient itself at a specific angle relative to gravity. With this construction, the first marker 32 allows conclusions to be drawn from the endoscopic image regarding the direction of the gravitational force. So as to be able to orient the retrieval container 5 correspondingly according to this information, the insertion instrument 6 comprises a second marker 34. This second marker 34 allows conclusions to be drawn from the endoscopic image regarding the orientation of the retrieval container 5. Making use of the endoscopic image, this orienting device 30 allows the retrieval container 5 already in its folded state to be oriented such that, subsequent to unfolding, the opening 2 of the retrieval container 5 is located in a desired position, for example, a position in which the opening 3 faces upwards.

In the illustrated embodiment of the orienting device 30, the first marker 32 is provided on the indicator ring 31 and the second marker 34 is provided on the insertion instrument 6 such that, in a position conducive to unfolding the retrieval container 5, the first marker 32 and the second marker 34 are aligned or located at the same position along the insertion instrument 6.

While various inventive aspects, concepts and features of the inventions may be described and illustrated herein as embodied in combination in the exemplary embodiments, these various aspects, concepts and features may be used in many alternative embodiments, either individually or in various combinations and sub-combinations thereof. Unless expressly excluded herein all such combinations and sub-combinations are intended to be within the scope of the present inventions. Still further, while various alternative embodiments as to the various aspects, concepts and features of the inventions—such as alternative materials, structures, configurations, methods, circuits, devices and components, software, hardware, control logic, alternatives as to form, fit and function, and so on—may be described herein, such descriptions are not intended to be a complete or exhaustive list of available alternative embodiments, whether presently known or later developed. Those skilled in the art may readily adopt one or more of the inventive aspects, concepts or features into additional embodiments and uses within the scope of the present inventions even if such embodiments are not expressly disclosed herein. Additionally, even though some features, concepts or aspects of the inventions may be described herein as being a preferred arrangement or method, such description is not intended to suggest that such feature is required or necessary unless expressly so stated. Still further, exemplary or representative values and ranges may be included to assist in understanding the present disclosure; however, such values and ranges are not to be construed in a limiting sense and are intended to be critical values or ranges only if so expressly stated. Moreover, while various aspects, features and concepts may be expressly identified herein as being inventive or forming part of an invention, such identification is not intended to be exclusive, but rather there may be inventive aspects, concepts and features that are frilly described herein without being expressly identified as such or as part of a specific invention. Descriptions of exemplary methods or processes are not limited to inclusion of all steps as being required in all cases, nor is the order that the steps are presented to be construed as required or necessary unless expressly so stated.

LIST OF REFERENCE SIGNS (1) Container
(2) Opening
(3) Closing member
(4) Connecting device
(5) Retrieval container
(6) Insertion instrument
(7) Shaft
(8) Operating member of the insertion instrument
(9) Structuring member
(10) Application instrument
(11) Connecting member of the insertion instrument
(12) Connecting member of the retrieval container
(13) Thread
(14) Loops
(15) Opening
(16) Grasping device
(17) Shaft of the application instrument
(18) Outer tube of the application instrument
(19) Operating member of the application instrument
(20) Chamber system
(21) Valve
(22) Filler neck
(23) Fluid conduit
(24) Connection member
(25) Outlet valve
(26) Outlet opening
(27) Sealing film
(28) Tube member
(29) Holding member
(30) Orienting device
(31) Indicator ring
(32) First marker
(33) Weight
(34) Second marker

We claim:

1. An endoscopic retrieval instrument for receiving and retrieving one or more objects from the human body, the instrument comprising:
   an insertion instrument;
   a retrieval container comprising an open top portion, a closed bottom portion and a wall between the open top portion and closed bottom portion, the open top portion being provided with a closing mechanism in the form of a thread which is passed through one of loops or apertures attached, wherein the loops or apertures are one of attached to or formed in the retrieval container, the closing mechanism selectively closing the open top portion at least partially;
   a coupling mechanism configured to selectively disconnect the retrieval container from the insertion instrument, wherein the retrieval container comprises a structuring member in the closed bottom portion configured to facilitate unfolding of the retrieval container into a predetermined shape without filling or inflating the structuring member with a fluid; and
   a separate connecting member fixedly connected to the outside of the wall of the retrieval container at a location between the open top portion and the structuring member, the separate connecting member being adapted to engage with the coupling mechanism independent and separate from the closing mechanism and wherein the separate connecting member is made of a flexible thin material comprising plastic film.

2. The endoscopic retrieval instrument according to claim 1, wherein the wall of the retrieval container between the open top portion at which the closing mechanism is arranged and the closed bottom portion at which the structuring member is arranged is made from a flexible thin material.

3. The endoscopic retrieval instrument according to claim 1, wherein the thread is configured to be at least partially guided out of a human body.

4. The endoscopic retrieval instrument according to claim 3, wherein the closing mechanism comprises a tube member through which the thread is guided at least partially.

5. The endoscopic retrieval instrument according to claim 1, wherein the retrieval container comprises a holding member configured to transmit a tensile force to the retrieval container.

6. The endoscopic retrieval instrument according to claim 5, wherein the holding member comprises another thread.

7. The endoscopic retrieval instrument according to claim 1, wherein the structuring member comprises a frame.

8. The endoscopic retrieval instrument according to claim 1, wherein the insertion instrument comprises an orienting device for indicating the direction of the gravitational force.

9. The endoscopic retrieval instrument according to claim 8, wherein the orienting device comprises a ring supported so as to be rotatable about a central axis of the insertion instrument, the ring having a center of gravity located outside the central axis.

10. The endoscopic retrieval instrument according to claim 9, wherein the ring comprises a first marker on an outside surface of the ring.

11. The endoscopic retrieval instrument according to claim 10, wherein the insertion instrument comprises a second marker on an outside surface, the second marker corresponding to a particular orientation of the retrieval container.

12. The endoscopic retrieval instrument according to claim 11, wherein the first marker and the second marker are arranged such that the position of the first marker has the same orientation as the second marker when the retrieval container has a desired orientation for its positioning in the human body.

13. The endoscopic retrieval instrument according to claim 1, wherein the separate connecting member is a looped thread being separate and distanced to the closing mechanism and also being configured to transmit, exclusively, a tensile force to the retrieval container.

14. A method for closing a retrieval container of an endoscopic retrieval instrument, the method comprising:
   providing an endoscopic retrieval instrument comprising an insertion instrument, a retrieval container comprising an open top portion, a closed bottom portion, a wall between the open top portion and closed bottom portion, and a structuring member in the closed bottom portion configured to facilitate unfolding of the retrieval container into a predetermined shape without filling or inflating the structuring member with a fluid, a coupling mechanism configured to selectively disconnect the retrieval container from the insertion instrument, the retrieval container including an opening portion thread which is passed through apertures in a wall of the retrieval container, the opening portion thread being operable to selectively at least partially close the open top portion, and a separate connecting member fixedly connected to the outside of the wall of the retrieval container at a location between the open top portion and the structuring member, the separate connecting member being adapted to engage with the coupling mechanism independent and separate from the opening portion thread, wherein the separate connecting member is made of a flexible thin material comprising plastic film;

providing an endoscopic application instrument comprising an operating member, a grasping device capable of being operated by the operating member, and an outer tube movable along a central axis of the application instrument, the outer tube being movable forward over the grasping device;

grasping the opening portion thread by means of the grasping device, and retracting the grasping device into the outer tube.

15. An endoscopic retrieval instrument for receiving and retrieving one or more objects from the human body, the instrument comprising:
   an insertion instrument;
   a retrieval container comprising an open top portion, a closed bottom portion, and a wall between the open top portion and closed bottom portion, the open top portion being provided with a closing mechanism in the form of a thread which is passed through one of loops or apertures attached, wherein the loops or apertures are one of attached to or formed in the retrieval container, the closing mechanism selectively closing the open top portion at least partially;
   a coupling mechanism configured to selectively disconnect the retrieval container from the insertion instrument, wherein the retrieval container comprises a structuring member in the closed bottom portion configured to facilitate unfolding of the retrieval container into a predetermined shape, and wherein the structuring member comprises a chamber system configured to be filled with a fluid, the chamber system comprising a first valve which, in a closed state, seals off against fluid contained in the chamber system and, in an open state, allows passage of a fluid into the chamber system; and
   a separate connecting member fixedly connected to the outside of the wall of the retrieval container at a location between the open top portion and the structuring member, the separate connecting member being adapted to engage with the coupling mechanism independent and separate from the closing mechanism, wherein the separate connecting member is made of a flexible thin material comprising plastic film.

16. The endoscopic retrieval instrument according claim 15, wherein the insertion instrument comprises a fluid conduit enabling a fluid to be conveyed from an extracorporeal part of the insertion instrument to a distal end of the insertion instrument.

17. The endoscopic retrieval instrument according to claim 15, wherein said insertion instrument comprises a mechanical coupling enabling a mechanical connection to the first valve to be established and wherein the insertion instrument comprises an operating member by means of which the mechanical connection of the insertion device to the first valve can be set.

18. An endoscopic retrieval instrument for receiving and retrieving one or more objects from the human body, the instrument comprising:
   an insertion instrument;
   a retrieval container comprising an open top portion, a closed bottom portion, and a wall between the open top portion and closed bottom portion;
   a coupling mechanism configured to selectively disconnect the retrieval container from the insertion instrument, wherein the retrieval container comprises a structuring member in the closed bottom portion configured to facilitate unfolding of the retrieval container into a predetermined shape, and wherein the structuring member comprises a chamber system configured to be filled with a fluid, the chamber system comprising an outlet valve which, in a closed state, seals off against fluid contained in the chamber system and, in an open state, allows passage of fluid out from the chamber system;
   a closing mechanism operable to selectively at least partially close an opening in the retrieval container, wherein the closing mechanism is connected to the outlet valve such that upon closure of the retrieval container, the outlet valve automatically assumes the open state; and
   a separate connecting member fixedly connected to the outside of the wall of the retrieval container at a location between the open top portion and the structuring member, the separate connecting member being adapted to engage with the coupling mechanism independent and separate from the closing mechanism, and wherein the separate connecting is made of a flexible thin material comprising plastic film.

\* \* \* \* \*